United States Patent
Miller et al.

(10) Patent No.: US 7,048,743 B2
(45) Date of Patent: *May 23, 2006

(54) METHODS FOR DELIVERING TISSUE IMPLANT MATERIAL WITH A HIGH PRESSURE APPLICATOR

(75) Inventors: Scott H. Miller, Sunnyvale, CA (US); Howard Preissman, San Jose, CA (US)

(73) Assignee: Arthrocare Corporation, Austin, TX (US)

( * ) Notice: Subject to any disclaimer, the term of this patent is extended or adjusted under 35 U.S.C. 154(b) by 414 days.

This patent is subject to a terminal disclaimer.

(21) Appl. No.: 10/310,354

(22) Filed: Dec. 4, 2002

(65) Prior Publication Data

US 2004/0249347 A1    Dec. 9, 2004

Related U.S. Application Data

(62) Division of application No. 09/408,690, filed on Sep. 30, 1999, now Pat. No. 6,783,515.

(51) Int. Cl.
*A61B 17/60* (2006.01)
(52) U.S. Cl. ...................................................... 606/94
(58) Field of Classification Search .................. 606/63, 606/92, 93, 94; 604/181, 187, 186, 218, 604/235, 131, 183, 219, 220, 221, 224
See application file for complete search history.

(56) References Cited

U.S. PATENT DOCUMENTS

| | | | |
|---|---|---|---|
| 29,083 | A | 7/1860 | Irving |
| 3,701,771 | A | 10/1972 | Almen et al. |
| 3,750,667 | A | 8/1973 | Pshenichny et al. |
| 3,882,858 | A | 5/1975 | Klemm |
| 3,919,773 | A | 11/1975 | Freeman |
| 4,189,065 | A | 2/1980 | Herold |

(Continued)

FOREIGN PATENT DOCUMENTS

DE    3443167    6/1986

(Continued)

OTHER PUBLICATIONS

Convey, et al., (1975). "The relative safety of polymethylmethacrylate" J. of Bone and Joint Surg. 57-A(1):57-64.

(Continued)

*Primary Examiner*—Sharon Kennedy
(74) *Attorney, Agent, or Firm*—Richard R. Batt; Raj Jaipershad

(57) ABSTRACT

This relates to an improved delivery system for accurately loading and controlling the delivery of flowable material to a patient. Particularly, the system may be used in the injection of hard tissue implant materials such as PMMA under pressures up to about 4000 psi. The system includes an applicator with a first column having an implant material introduction section adapted to provide for effective loading of the implant material and a second column housing a piston. The introduction section has a larger size than that of a vessel section or bore in which the requisite pressure seal between the piston and bore wall is formed. The first column may include an introduction section flared open to an included larger funnel-like opening or a separate funnel may be used that interfaces with the introduction section to facilitate the introduction of implant material. Handles on the first and second columns to be turned relative to each other to advance the columns toward each other may be provided for manual actuation of the applicator to drive implant material through a cannula and deliver implant material to a desired site.

16 Claims, 8 Drawing Sheets

U.S. PATENT DOCUMENTS

| | | | |
|---|---|---|---|
| 4,274,163 A | 6/1981 | Malcom et al. | |
| 4,288,355 A | 9/1981 | Anderson et al. | |
| 4,312,343 A | 1/1982 | Leveen et al. | |
| 4,341,691 A | 7/1982 | Anuta | |
| 4,364,921 A | 12/1982 | Speck et al. | |
| 4,373,217 A | 2/1983 | Draenert | |
| 4,404,327 A | 9/1983 | Crugnola et al. | |
| 4,469,109 A | 9/1984 | Mehl | |
| 4,554,686 A | 11/1985 | Baker | |
| 4,610,692 A | 9/1986 | Eitenmuller et al. | |
| 4,637,931 A | 1/1987 | Schmitz | |
| 4,653,489 A | 3/1987 | Tronzo | |
| 4,670,008 A | 6/1987 | Von Albertini | |
| 4,671,263 A | 6/1987 | Draenert | |
| 4,728,570 A | 3/1988 | Ashman et al. | |
| 4,791,150 A | 12/1988 | Braden et al. | |
| 4,793,363 A | 12/1988 | Ausherman et al. | |
| 4,795,444 A | 1/1989 | Hasegawa et al. | |
| 4,798,596 A | 1/1989 | Muhlbauer | |
| 4,815,454 A | 3/1989 | Dozier, Jr. | |
| 4,837,279 A | 6/1989 | Arroyo | |
| 4,838,282 A | 6/1989 | Strasser et al. | |
| 4,900,546 A | 2/1990 | Posey-Dowty et al. | |
| 4,929,238 A | 5/1990 | Baum | |
| 4,966,601 A | 10/1990 | Draenert | |
| 4,969,888 A | 11/1990 | Scholten et al. | |
| 5,014,717 A | 5/1991 | Lohrmann | |
| 5,015,101 A | 5/1991 | Draenert | |
| 5,112,354 A | 5/1992 | Sires | |
| 5,195,526 A | 3/1993 | Michelson | |
| 5,265,956 A | 11/1993 | Nelson et al. | |
| 5,282,861 A | 2/1994 | Kaplan | |
| 5,304,586 A | 4/1994 | Hammesfahr et al. | |
| 5,336,263 A | 8/1994 | Ersek et al. | |
| 5,336,699 A | 8/1994 | Cooke et al. | |
| 5,341,816 A | 8/1994 | Allen | |
| 5,344,232 A | 9/1994 | Nelson et al. | |
| 5,346,495 A | 9/1994 | Vargas, III | |
| 5,367,002 A | 11/1994 | Huang et al. | |
| 5,372,583 A | 12/1994 | Roberts et al. | |
| 5,415,474 A | 5/1995 | Nelson et al. | |
| 5,431,654 A | 7/1995 | Nic | |
| 5,451,406 A | 9/1995 | Lawin et al. | |
| 5,456,267 A | 10/1995 | Stark | |
| 5,476,880 A | 12/1995 | Cooke et al. | |
| 5,507,813 A | 4/1996 | Dowd et al. | |
| 5,558,136 A | 9/1996 | Orrico | |
| 5,571,182 A | 11/1996 | Ersek et al. | |
| 5,574,075 A | 11/1996 | Draenert | |
| 5,599,315 A | 2/1997 | McPhee | |
| 5,653,730 A | 8/1997 | Hammerslag | |
| 5,658,332 A | 8/1997 | Ducheyne et al. | |
| 5,660,186 A | 8/1997 | Bachir | |
| 5,676,146 A | 10/1997 | Scarborough | |
| 5,681,872 A | 10/1997 | Erbe | |
| 5,718,707 A * | 2/1998 | Mikhail | 606/94 |
| 5,792,478 A | 8/1998 | Lawin et al. | |
| 5,795,922 A | 8/1998 | Demian et al. | |
| 5,797,679 A | 8/1998 | Grulke et al. | |
| 5,800,405 A | 9/1998 | McPhee | |
| 5,925,051 A * | 7/1999 | Mikhail | 606/94 |
| 6,019,747 A | 2/2000 | McPhee | |
| 6,042,262 A | 3/2000 | Hajianpour | |
| 6,176,607 B1 | 1/2001 | Hajianpour | |
| 6,217,581 B1 * | 4/2001 | Tolson | 606/86 |
| 6,582,446 B1 * | 6/2003 | Marchosky | 606/167 |
| 6,676,664 B1 * | 1/2004 | Al-Assir | 606/94 |
| 6,770,079 B1 * | 8/2004 | Bhatnagar et al. | 606/94 |
| 2004/0215202 A1 * | 10/2004 | Preissman | 606/94 |

FOREIGN PATENT DOCUMENTS

| | | |
|---|---|---|
| DE | 42 19 563 A1 | 12/1993 |
| EP | 0261182 | 3/1988 |
| WO | WO 92/04924 | 4/1992 |
| WO | WO 97/04657 | 2/1997 |

OTHER PUBLICATIONS

Cotton, et al. (1996) "Preoperative percutaneous injection of methyl methacrylate and N-Butyl cyanoacrylate in vertebral hemangiomas," Am. J. Neuroradio 17:137-142.

Cybulski (1989). "Methods of surgical stabilization for metastatic disease of the spine", Neurosurgery 25:250-252.

Deramond, et al., (1990) "Percutaneous vertebroplasty with methyl-methacrylate: technique, method, results," Radiology 117(supp.):352.

Dierks, et al., (1992). "Treatment of an infected mandibular graft using tobramycin-impergnated methylmethacrylete beads: Report of a case" J. Oral Maxillofac Surg 50:1243-1245.

Galibert, et al., (1987). "Note preliminarie sur let traitement des angiomes vertebraus par vertebroplastie acrylique percutanee," Neurochirurgie 33:166-168 (Partial summary translation included.).

Goode, et al., (1992). "Tobramycin-impregnated methylmethacrylate for mandible reconstruction," Arch Otolaryngol Head Neck Surg 118:2201-204.

Harrington (1986). "Anterior decompression and stabilization of the spine as a treatment for vertebral collapse and spinal cord compression from metastatic malignancy," Clin. Orthopedics and Related Research pp. 177-197.

Kaemmerlen, et al. (1989). "Vertebroplastie percutanee dans le traitement des metastase," J. Radiol. 70(10):557-562. (Partial summary translation included).

McLaughlin, et al., (1973). Blood clearance and acute pulmonary toxicity of methylmethacrylate in dogs after simulated arthorplasty and intravenous injection,: J. of Bone and Joint Surg. 55-A(8):1621-1628.

Nicola, et al. (1987). "Vertebral hemangioma: Retrograde embolization—Stabilization with methyl methacrylate," Surg Neurol 27:481-486.

O'Donnell, et al. (1984) Recurrence of giant-cell tumors of the long bones after curettage and packing with cement,: J. of Bone and Joint Surg. 76-A(12):1827-1833.

Persson, et al., (1984). "Favorable results of acrylic cementation for giant cell tumors," Acta Orthop Scand 55:209-214.

Phillips, et al. (1971). "Cardiovascular effects of implanted acrylic bone cement," British Medical Journal 3:460-461.

Shapiro (1991). "Cranioplasty, vertebral body replacement, and spinal fusion with tobramycin-impregnate methylmethacrylate," Neurosurgery 28(6):789-791.

Stringham, et al., (1994). "Percutaneous transpedicular biopsy of the psine," Spine 19(17):1985-1991.

Sundaresen, et al. (1985). "Treatment of neoplastic epidural cord compression by vertebral body resection and stabilization," J. Neurosurg. 63:676-684.

Wang, et al., (1984). "Safety of anterior cement fixation in the cervical spine: In vivo study of dong spine," So. Medical J. 77(2):178-179.

Weill, et al., (1996). "Spinal Metastasis: Indications for and Results of Percutaneous Injection of Acrylic Surgical Cement," Radiology 199(1):241-247.

* cited by examiner

METHODS FOR DELIVERING TISSUE IMPLANT MATERIAL WITH A HIGH PRESSURE APPLICATOR

CROSS REFERENCE TO RELATED APPLICATION

This is a divisional of application Ser. No. 09/408,690, filed Sep. 30, 1999, entitled "High Pressure Delivery System" now U.S. Pat. No. 6,783,515.

TECHNICAL FIELD

The present invention relates to a system for more accurately controlling the delivery of flowable material to a patient. Particularly, the system may be used in the injection of hard tissue implant materials. Features of the invention provide for effective loading of an applicator configured to generate high fluid delivery pressures.

BACKGROUND OF THE INVENTION

The introduction of flowable material to an implantation site within a patient to effect one or more therapeutic goals is well known. The flowable material itself may be of high or low viscosity. Matter ranging from typical fluids or solutions to non-Newtonian fluids, pastes, gels and the like has been used for one purpose or another in the medical arts.

It is well-recognized that syringes may be used for percutaneous delivery or injection of flowable material. However, such devices are of limited value in the delivery of high viscosity fluids. In general, users are only capable of generating pressures of about 100–150 psi with 10 cc syringes. This places a limitation on the viscosity of the flowable material that can be effectively "pushed through" the syringe and attached needle or cannula and fully delivered to a treatment site. The use of a small barrel syringe, e.g., a 1 cc syringe enables the user to generate higher driving pressures (e.g., pressures of 800 psi and possibly as high as 1000–1200 psi) that may be used to flow a viscous implant material. However, the 1 cc volume of the syringe may be very limiting as to the amount of material deliverable to a patient. This can be especially problematic when the material to be injected is a settable composition where (for various reasons) it is important to deliver all the material desired in a single "shot". Another problem with a 1 cc syringe is lack of control, as high pressures are generated in a "spike-like" response time and are not continuously controllable.

Other devices used in the medical arts do not suffer such a control problem by virtue of a threaded arrangement used to advance a piston head within a bore to drive material from a loaded device. U.S. Pat. No. 29,083 to Irving discloses a syringe having a plunger with a screw thread on its exterior. Advancing the plunger by turning it relative to a housing generates sufficient pressure to force a semi-solid ointment out of a perforated tube. This applicator, however, is only configured for rectal delivery of a hemorrhoid medicament.

By contrast, U.S. patent application Ser. No. 09/053,108, "Pressure Applicator for Hard Tissue Implant Material," by Preissman, Filed Apr. 1, 1998 and U.S. Pat. No. 6,383,190, "High Pressure Applicator" by Preissman, Filed on Sep. 30, 1999, each incorporated by reference herein as part of the invention, disclosed high pressure applicators utilizing two threaded columns in various arrangement capable of use for injecting material in useful procedures.

While the applicator of the earlier-filed patent application by Preissman does not provide some of the advantages of the present invention (particularly in loading implant material), the applicators disclosed in each patent application are of practical utility as high-pressure applicators for use in percutaneous vertebroplasty. In this procedure, once a cannula is positioned in the cancellous bone of a vertebrae, a hard tissue implant material such as Polymethylmethacrylate (PMMA) is injected into a site for treatment to reinforce and solidify the damaged hard tissue.

Generally, about 3.5 cc of implant material per side of the vertebral body is required. Control issues aside, this makes the use of a 1 cc syringe problematic. Basically, a vertebroplasty procedure would require multiple reloading steps with such a syringe. Further, the additional time spent for such action would result in more than mere inefficiency. Reloading time is time spent while an implant material like PMMA is polymerizing to become increasingly viscous beyond a state in which it may be safely or effectively delivered by any type of injection device, regardless of its high-pressure capacity. Both the need to inject the implant material through a relatively narrow needle or cannula and the fact that the desired site is relatively closed (i.e., trabecular bone) compounds material thickening effects which make "single shot" delivery ability important.

While PMMA in a nearly-solidified state is inappropriate for use with the present invention, a highly-viscous or syrupy consistency of PMMA is generally believed to be most advantageous for performing percutaneous vertebroplasty. Such a consistency insures that the implant material stays in place much better than a less viscous, more flowable material.

It is known that leakage or seepage of PMMA from a vertebral implant site or extravasation through fractures in the bone can cause a host of complications—some of which can be very serious and even result in death. For example, Weil et al. reported cases of sciatica and difficulty in swallowing which were related to focal cement leakage, *Radiology* 1996; Vol. 199, No. 1, 241–247. A leak toward the distal veins poses an even more serious risk, since this can cause a pulmonary embolism which is often fatal.

In addition to leakage around the cannula and through bone, overfilling of the intended implant site can result in introduction of implant material into the blood stream after removal of the cannula from the implant site. Due to the high pressures involved in the implant procedure, compliance within the delivery system can act as a capacitance under pressure thereby storing a volume of the implant material and energy under pressure which, upon release of the pressure, drives an undesired additional amount of implant material into the implant site to cause potentially-dangerous overfilling. This additional amount of outflow is sometimes referred to as "oozing" or "drip". System compliance may also result in decreased response performance of the delivery system.

Compliance may be introduced into a system either by virtue of appreciable elasticity of tubing, by other members forming part of the delivery system or by air bubbles introduced in the filling or loading of the applicator with implant material. Purging of air from a system loaded with highly-viscous matter may be difficult or impossible especially where air bubbles are not initially only near the system's outlet. This is because air bubbles will simply not be able to buoy to a point where they may be ejected without extruding a large volume of the implant material intended for implantation from the applicator.

Specific adaptation for venting or purging of air from a syringe for delivering viscous material is disclosed in U.S. Pat. No. 4,795,444 to Hasegawa et al. In this device, space is provided in a top section of the syringe so that an end of a plunger may pass through material in the top section to vent air bubbles before forming a seal in the smaller diameter bottom section of the syringe. The differential in sizes of the sections may be provided in stepwise fashion, as a tapered wall or as by a recessed channel. All this being said, as stated previously—a syringe is of limited utility or practicality as a high pressure applicator and cannot be effectively used as an applicator in the present invention due to various shortcomings inherent to the limitations of syringes as discussed above.

Accordingly, especially for use with PMMA in percutaneous vertebroplasty procedures, there exists a need for an improved system able to provide substantially non-compliant and precise application of implant material under high pressures to a desired location in a single batch. The system of the present invention includes method and apparatus adapted to meet such needs as well as provide other advantages readily apparent to those with skill in the art.

SUMMARY OF THE INVENTION

The present invention is an improved system for controlled delivery of injectable material to a patient. It includes a first column including a vessel section open to an implant material introduction section. A second column is provided which is drivably engageable with the first column along an advancement axis. Handles may be provided on the first and second columns for manual actuation of the device by turning the columns relative to each other where a threaded interface is provided. A piston or plunger member is provided and advances within the vessel section of the first column upon advancement of the second column to generate pressure to drive implant material loaded within the vessel section. Although a close-tolerance or slight interference fit between the piston and the vessel section may be provided to develop a seal, it is preferable to provide an O-ring or other sealing element as typically done in the art.

The introduction section of the first column has a slightly larger cross-sectional area than that of the portion of the vessel section adjacent to it. Providing a larger size or diameter introduction section than vessel section entrance enables the introduction of the piston into the implant material without simultaneously forming a seal where compliant bubbles may be trapped. Put another way, the differential in sizes is provided so that when the vessel section is fully filled and the introduction section is at least partially filled, the end of the piston may be dipped in the implant material to allow for the exclusion of air bubbles prior to driving it into the vessel section.

Where the implant material is less viscous, the piston may merely be plunged in to implant material in the introduction section and driven into the vessel section. Where the implant material is more viscous, it may be advisable to more carefully place the piston in contact with the implant material in the introduction section to avoid air bubbles (by turning, rocking or otherwise manipulating the piston) and then inserting it into the vessel section where a seal is formed.

The introduction section of applicator in the present invention may be relatively close in size to the vessel section entrance to provide only a surrounding dam for a meniscus poured over the vessel section. Since the amount of material to be provided in the introduction section need not be great to facilitate the venting or purging as described above, in using the invention it is better to only introduce slightly more implant material than will fill the vessel. Introduction of a larger amount of implant material is not only wasteful, but may result in material drainage out of the introduction section into other parts of the applicator—especially when the applicator is inverted or turned as will often be the case in preparing PMMA implant material for delivery.

To help account for the possibility of excess implant material and associated potential of fouling of the applicator by such excess, a larger size of the introduction section than strictly required for the venting feature discussed above may be used to act as a catch basin for implant material. This will provide an increased margin of error in pouring implant material into the applicator before overflowing the introduction section. Further, the walls of such an enlarged catch basin may help to prevent contamination of the applicator by virtue of adherence of the implant material to the surface area provided during inversion or agitation of the applicator.

The present invention may include a funnel or increased-size target region integrated into the first column, adjacent to the introduction section, to aid in pouring implant material into the applicator. Drive threads may be placed on the exterior of the funnel section. However, when no integral funnel is provided, drive threads may be placed exterior to the introduction section which may be of a finer pitch or higher thread count than those on a larger diameter. A smaller diameter and/or finer threads will provide for greater mechanical advantage for generating higher driving pressures more easily. To help in loading material into the applicator when no integral funnel is used, a separate funnel element may be provided to interface with the introduction section.

The present invention includes such features of the pressure applicator discussed above as well as the methods involved in preparing and using the applicator to inject material into a patient. Such methods or procedures involve preparing an applicator by at least partially filling an introduction section with a material for delivery above a level at which a piston may form a seal and driving a piston head into a vessel section bore where a seal is formed without the introduction of compliant matter such as air bubbles. The preparation method may be followed by introducing material from the applicator into a patient in a medical procedure that may be distinct and separate from the inventive preparation method.

The invention also includes those concomitant parts or elements useable with the applicator in delivering material to a site within a patient. Such elements may include a delivery hose, a cannula (alone or in combination with one or more stylets) and vertebroplasty implant material. Reference is made to preferred embodiments of these elements which are described in further detail below. Together, these elements may form part of the inventive kit or system to be used in a procedure or method as variously described herein.

BRIEF DESCRIPTION OF THE DRAWINGS

Each of the following figures diagrammatically illustrates aspects of the present invention. No aspect shown is intended to be limited to the expression pictured.

DETAILED DESCRIPTION OF THE INVENTION

An example procedure for using precision instruments according to the present invention in an intravertebral vertebroplasty will now be described. It is expressly noted, however, that this invention is useable in a myriad of other procedures where virtually any flowable material to be delivered to a patient under pressure is employed. But for percutaneous vertebroplasty, initially a surgeon identifies a landmark with the aid of fluoroscopy or other imaging technique. Next, an injection is given to anesthetize the skin where insertion will occur. A long needle, having a length sufficient to percutaneously access the periosteum of the target vertebra is then used to inject anesthesia subperiostially.

Figure 1:
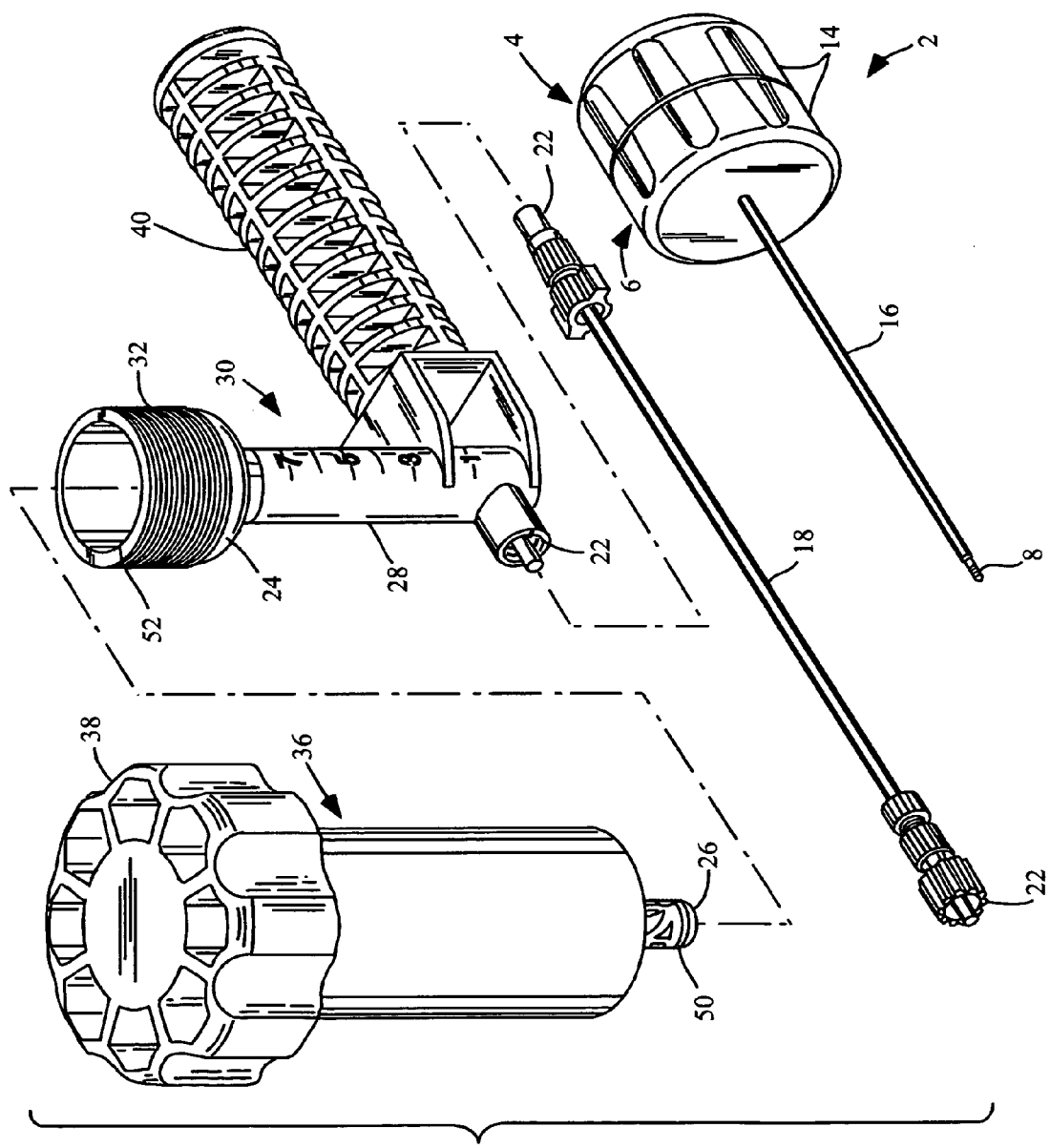
FIG. 1 shows the primary components of the inventive flowable implant material delivery system and indicates the manner in which they are assembled.

After sufficient time has passed to effectively anesthetize the skin, an incision is made through the skin with a scalpel. A combined stylet and cannula 2 (such as stylet 4 and cannula 6 threaded together, as shown in FIG. 1) and further described in U.S. patent Ser. No. 09/409,984, "Precision Instruments For Use In Vertebroplasty" by Preissman et al., filed on Oct. 14, 1997 and "Precision Depth Guided Instruments for Use In Vertebroplasty", U.S. Pat. No. 6,033,411 filed Oct. 14, 1997, incorporated by reference, are then inserted through the incision and advanced using a translation motion with not torquing, until the tip 8 of the stylet abuts the cortical bone of the vertebra or the perisosteum surrounding it. Once contact has been made, the cannula tube is then grasped with a pair of hemostats and fluoroscopy/imaging is used to access the position of the cannula/stylet with regard to the vertebra. The hemostats are used to allow the hands of the user to be removed for the filed in which the imaging radiation will be applied. With the aide of medical imaging, the cannula/stylet 2 are positioned with respect to the pedicle of the vertebra at the desired orientation for passing therethrough and into the body of the vertebra. Imaging may be performed both perpendicular to the longitudinal axis of the spine/vertebra, as well as along the longitudinal axis of the cannula/stylet, or at an angle to the longitudinal axis of the cannula stylet.

Figure 3:
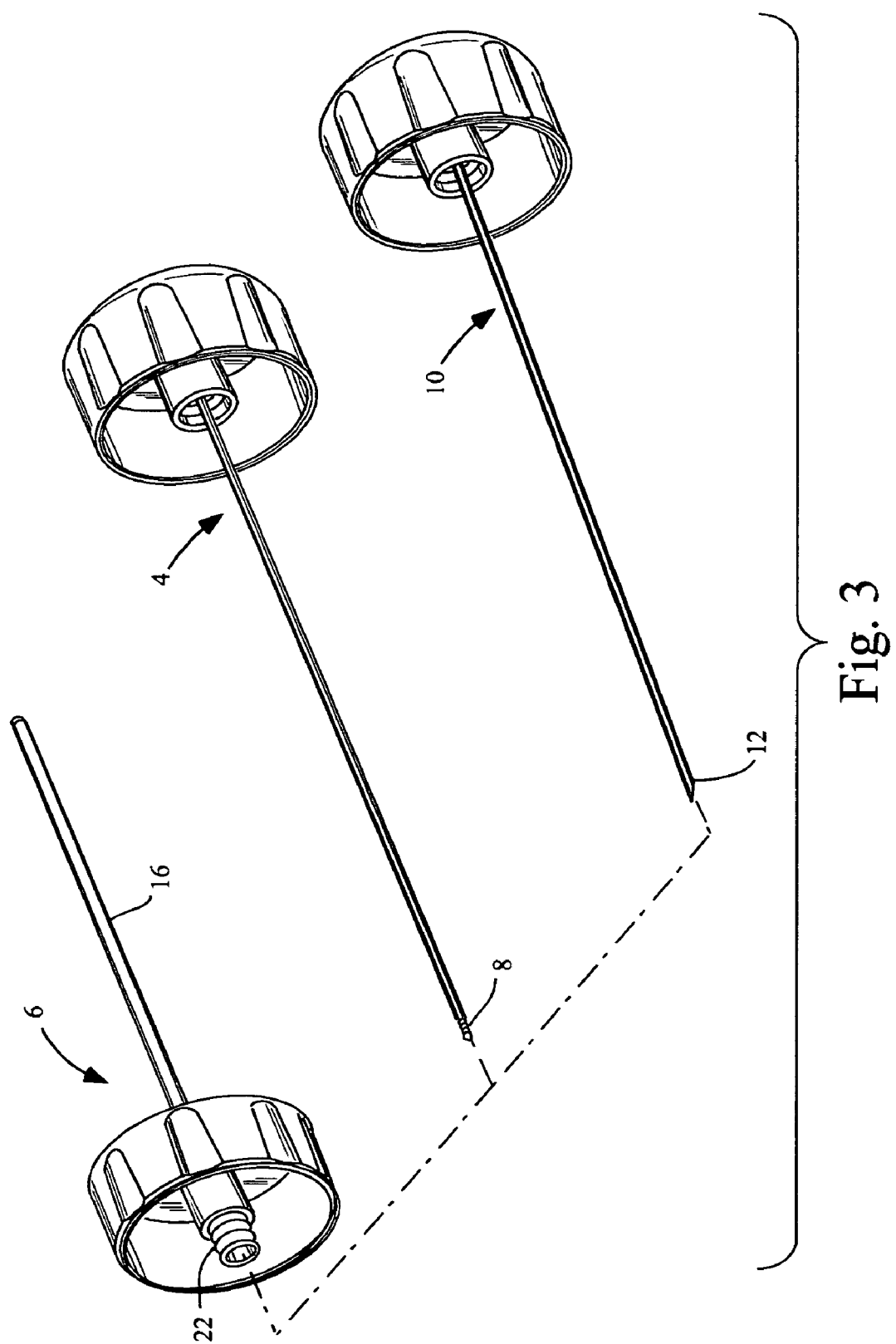
FIG. 3 show the cannula and two types of stylets useable in the invention and indicates the manner in which they are assembled.
Figure 4A:
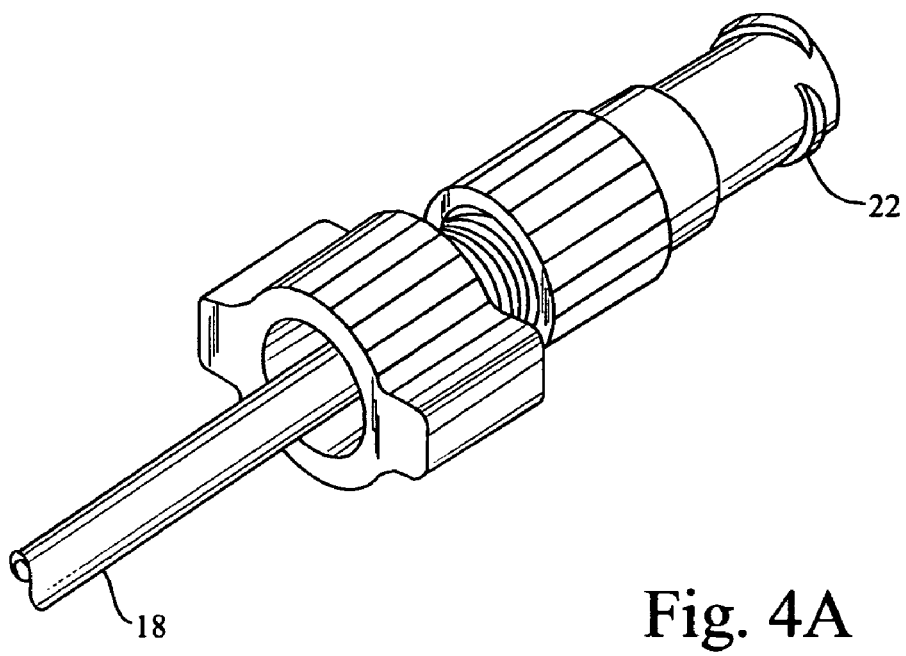
FIGS. 4A and 4B show views of the ends of a hose and connectors useable in the invention.
Figure 4B:
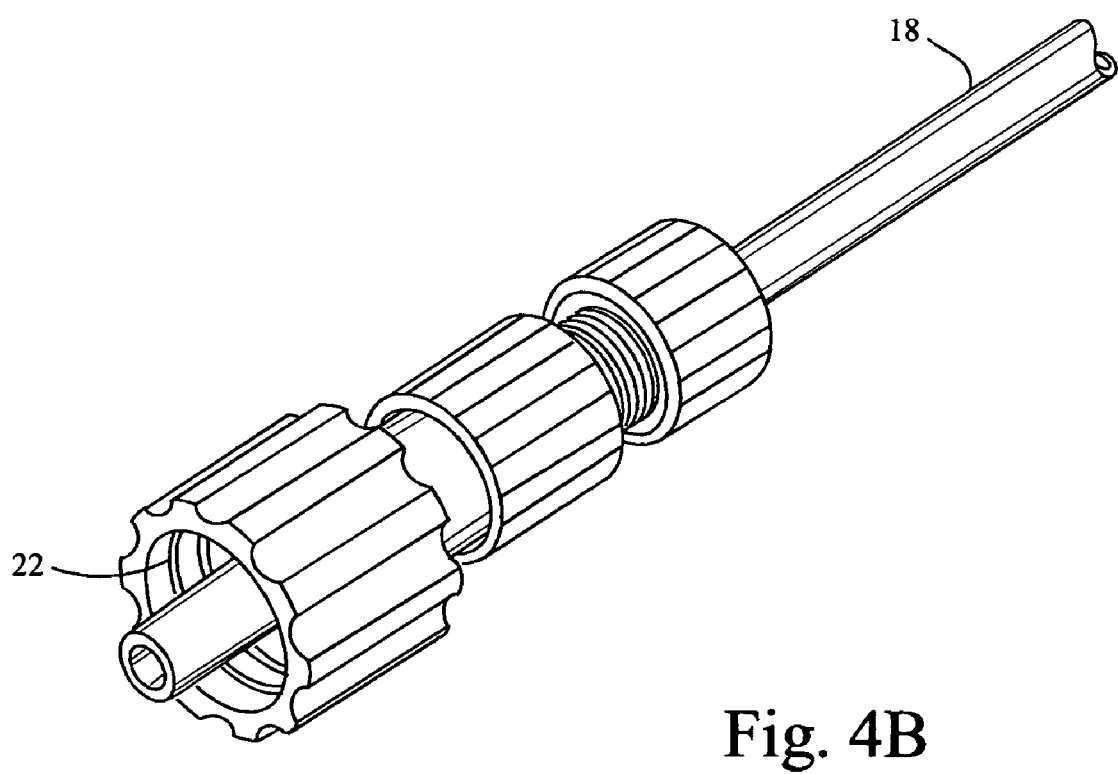

If the advancement of the stylet and cannula does not proceed along the intended pathway, the stylet 4 may be reverse rotated while preventing rotation of the cannula 6 to maintain it in position and remove the stylet. A second stylet 10, as shown in FIG. 3, which has an asymmetric tip 12 may then be inserted into the cannula and connected therewith. Stylet 10 is configured essentially identically to stylet 4 with the exception of the distal end thereof. Rather than a pointed and threaded tip portion, stylet 10 is provided with a beveled tip portion 12. A preferred angle of orientation of the beveled surface is about 30° with respect to the longitudinal axis of the stylet, although this angle may be varied to include any acute angle to give various responses in directional steering of the stylet 10.

Yet another stylet may be included which as other double-beveled or diamond-shaped tip portion adapted to pass through the cannula. Still further, stylets having conical or pyramidal type tip portions having a substantially smooth surface may be additionally or alternatively provided. All of these stylets may be useful for improved "targeting" ability in initially piercing skin or hard tissue. Other uses, advantages and more detailed description of variations of each of the stylets advantageously useable in the present system are described in "Precision Instruments for Percutaneous Delivery of Implant Materials" U.S. Ser. No. 09/409,984 filed on Oct. 14, 1997, which is herein incorporated by reference, especially as to that disclosure. The operator can rotate the stylet 10 to position the tip 12 in a direction toward which he/she wishes to migrated the stylet 10. Once the orientation of the stylet 10 and cannula 6, having been advanced over the stylet 10, has been satisfactorily set, the fluoroscopy/imaging is discontinued, the hemostats are removed and the operator carefully grasps the cannula/stylet being careful not to alter the orientation. Stylet 10 with the beveled tip 12 is then removed and replaced by stylet 4 with self-tapping threads 8. Grasping the combination handle 14, and optionally the cannula tube 16, the operator then proceeds to both push translationally and torque the combination handle to begin threading the stylet 4 into the cortical bone.

After "biting" into the bone with a few turns of the self-tapping threads 8, the operator's hands are removed and the devices maintain their position by the support provided by the bone surrounding the threads. The devices/instruments are again viewed fluoroscopically or otherwise imaged both along the longitudinal axis of the cannula/stylet and laterally to determined the depth of the instruments. If the desired depth and placement has not yet been achieved, imaging is discontinued, and the cannula/stylet are further torqued or otherwise advanced into the cancellous bone until the tip of the cannula has been positioned in a desirable location.

Upon achieving the desired placement of the cannula at a site for treatment, the operator reverse rotates the stylet 4 to remove it from the cannula 6, while preventing rotation of the cannula 6. The cannula at this stage is effectively press-fit into the bone site which aids the operator in preventing its rotation. Once the stylet has been completely removed from the cannula, fluoroscopic imaging/viewing of the cannula may optionally be performed to assure that the cannula did not move during the removal of the stylet.

Optionally, a contrast agent, e.g. a product known as OMNIPAQUE 300 available from Nycomed in Princeton, N.J., may be injected through the cannula and the flow of the contrast agent is viewed fluoroscopically or with other imaging in order to ascertain that the tip of the cannula has not been placed in a vein or other significant vessel. Preferably the contrast agent is injected through tubing connected to the cannula. When tubing is used, it is preferably of a smaller length and diameter than tubing that is used for injection of implant material. Contrast agent must be flushed out of the vertebra prior to injection of the implantation material, so it is preferable to inject a small volume of the contrast agent. Viewing of the flow of the contrast agent helps to identify the shape of the vertebral body into which the injection of implant material is to be performed, as well as to locate where the major veins lie. After completing the flow of the contrast agent, the remnants of the contrast agent are flushed out of the vertebral body by injecting a flushing solution (e.g., saline) through the cannula 6, using a syringe or other injector. The imaging is preferably discontinued for this step. It is preferable to use a minimum amount of contrast agent. The contrast agent is flushed out so that it does not occlude, cloud, or otherwise compete with the viewing of the radiopacity of the implant material when it is placed.

The cannula 6 at this point will be filled with saline. If not filled by saline by such flushing, then it may be backfilled. The substantially non-compliant conduit 18, if used, may be connected to the pressure applicatior 20 and have implant material forced through it prior to being attached to the cannula 6. An example of an implant material for vertebroplasty is a PMMA bone cement containing contrast agents including radiographic powder or particles of any typical material such as U.S.P. Barium Sulfate and/or tracer particles. Aspects of acceptable implant material are described in U.S. Pat. No. 6,019,776, "Enhanced Visibility Materials For Implantation In Hard Tissue" by Preissman, filed Oct. 14, 1997.

Luer fitting/locks 22 may be used to provide a high pressure capacity connection between the respective members of the inventive system. A detailed description of a high pressure, noncompliant conduit or tubing 18 which can be used in this invention is given in the copending commonly assigned U.S. patent application Ser. No. 09/276,062, "Non-Compliant System For Delivery Of Implant Material" by Preissman, filed Mar. 24, 1999, which is hereby incorporated by reference thereto, in its entirety.

Non-compliance of the system is further achieved by loading of the applicator 20 to avoid the introduction of air bubbles as contemplated by the present invention. Such loading is provided for by means of plunger head 26 smaller in size than an introduction section 24 so it may freely pass through the introduction section as it is introduced into a vessel section 28 where a frictional seal may be formed. In the embodiment of the invention shown in the figures, round members are used for the piston head 26, vessel section 28 and the introduction section 24 of first column 30. It is noted, however, that any advantageous geometry may be used for the vessel section 28. It is preferable that at least a portion of the first column 30 be round though, since threads 32 may then be placed on its exterior to engage with mating threads 34 (FIG. 7A) on the interior of second column 36.

When a different manner of drivably engaging first column 30 relative to the second column 36 is desired (e.g., a ratcheting interface, or a pneumatic or hydraulic driven arrangement) a round shape of the introduction section 24 may be less preferred. Other drive mechanisms or embodiments of interest which may be used in the present invention are also discussed in U.S. Pat. No. 6,019,776, "Precision Depth Guided Instruments for Vertebroplasty" filed Oct. 14, 1997, and U.S. patent application Ser. No. 09/409,984, "Precision Instruments For Use In Vertebroplasty" filed on Oct. 14, 1997, each by Pressman and herein incorporated by reference in their entireties.

Where the first column 30 and second column 36 are configured for threaded engagement to be driven towards or away from each other, it is advantageous to provide handles 38 and 40 on the columns. The handles may be integrally formed or merely affixed in some matter. Preferably, handle 40 on the first column 30 is in the form of a radially-extending arm. This may serve as a stabilizer when a knob-like grip 38 is turned. Such actuation of the applicator 20 will avoid twisting the conduit 18 or cannula 6 during the delivery of material.

Where threads are used or torsional movement is translated into axial movement of the columns 30 and 36 toward each other otherwise, it will be advantageous to provide an enlarged base 44b of the piston/plunger rod 44 with an end 44d having a spherical surface which is free to rotate with respect to the inner end surface 36d of the second column 36. The enlarged base 44b is held in position by the placement of one or more (preferably two) internal retaining rings 42 which engage within a recess in second column 36 and abut the enlarged base 44b to substantially prevent translational movement thereof with respect to the second column 36. Thus the rod 44 will not fall out of the second column 36 when inverted or otherwise jostled, but the rod 44 is still allowed to turn relative to the column 36.

Such turning relative to the housing 36 will be advantageous especially when using gritty implant material to help preserve seal 50 since it may merely translate within the pressure vessel 28 rather than rotate through its translation. The retaining member 42 may comprise one or more star-shaped internal retainers, for example, as shown in FIG. 7B, or the like.

The various portions of the pressure applicator 20 may be sized to provide sufficient mechanical advantage to enable the application of pressures up to about 4000 psi by hand. As alluded to variously, mechanical advantage of the system is determined in large part by handle size 38, 40, the bore size or the vessel section 28, and the mechanical advantage of the drive means. In the embodiments shown, threadings are provided on the exterior of the first column 30 and interior of the second column 36. Manufacturing and material considerations, and the diameter on which to place the threads will determine the thread pitch which may be used. This in turn determines the mechanical advantage of the drive means. Where a greater mechanical advantage is desired, a finer thread pitch will provide the same. Also, the diameter of threaded sections of the columns 30 and 36 may be decreased. Alternately, a finer pitch thread may be used on a relatively larger diameter section by changing material or manufacturing procedure (such as cutting the threads into the respective members rather than molding the pieces as is presently preferred). In all, a pressure applicator produced according to the present invention is a balancing of various design goals relating to performance and cost.

Figure 2:
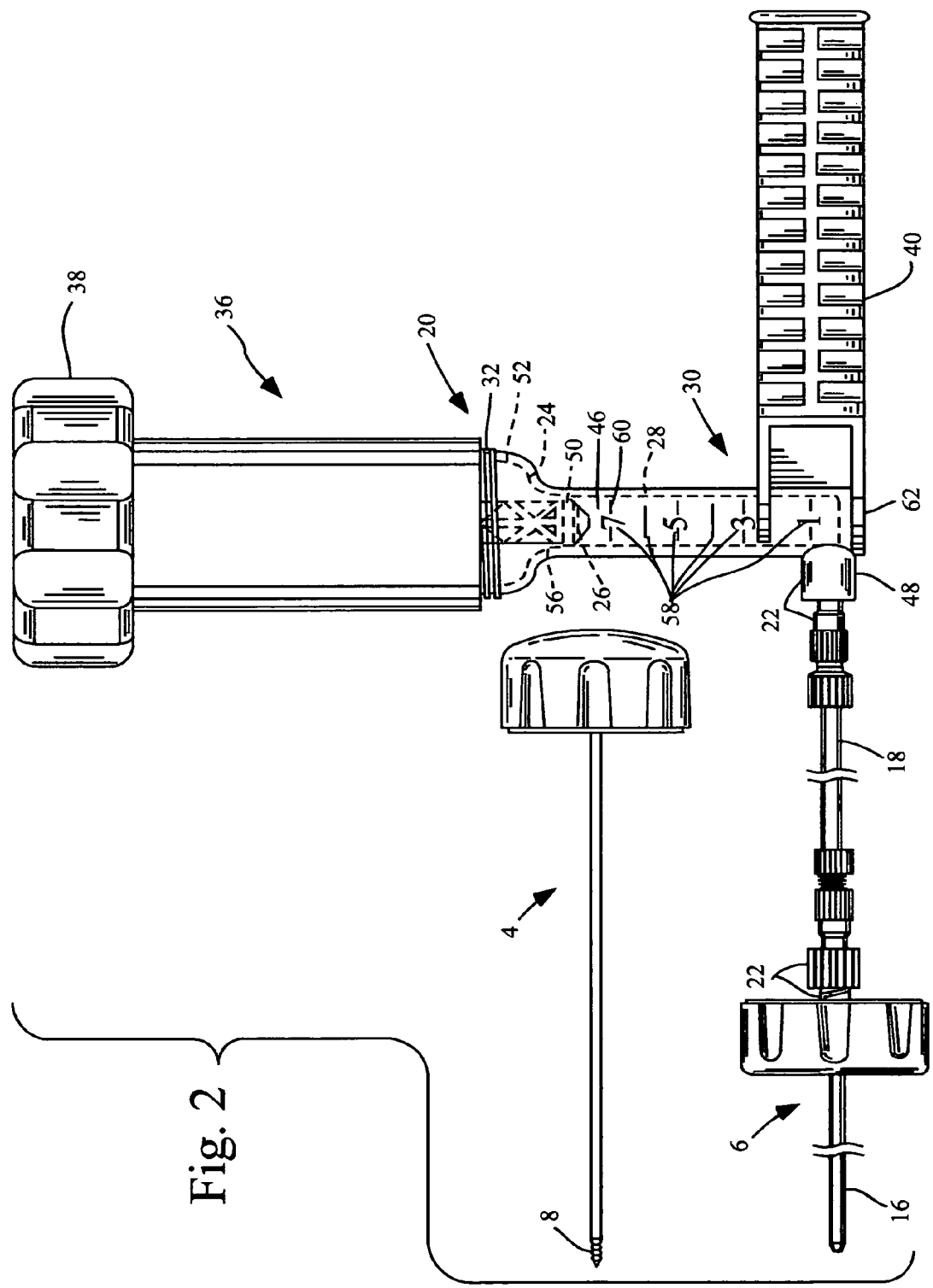
FIG. 2 shows the implant delivery components assembled and prepared for use.
Figure 5:
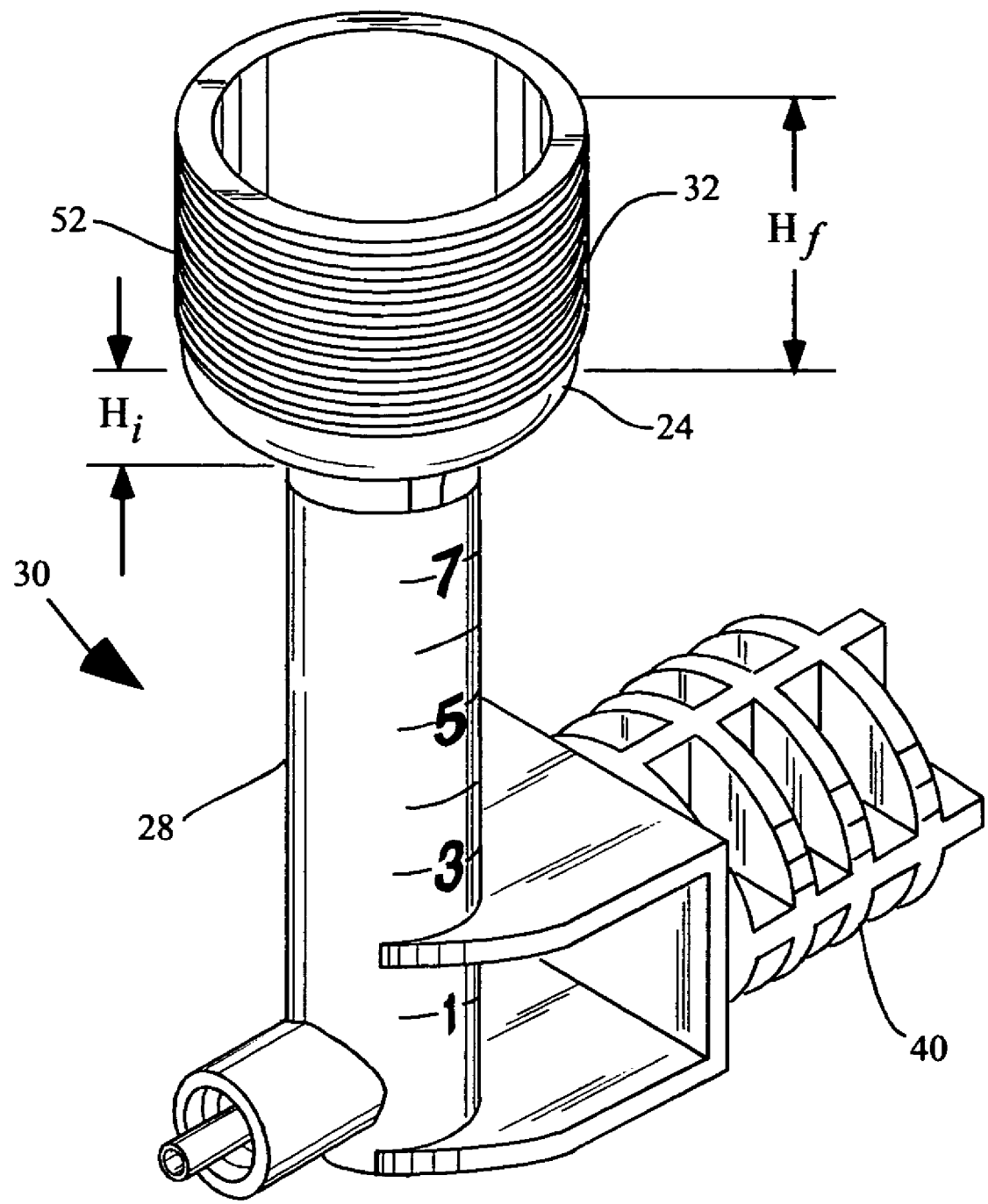
FIG. 5 shows a first column including an integrated funnel section.
Figure 6:
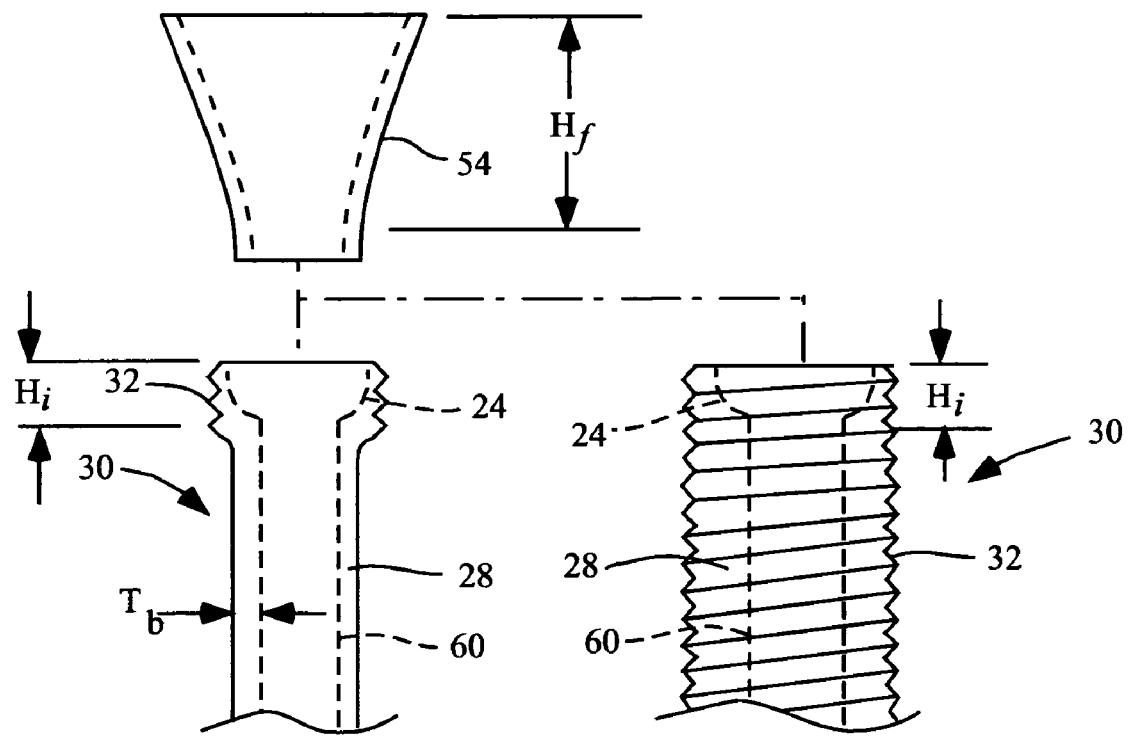
FIG. 6 shows alternate first columns and an independent funnel useable with each.

In the embodiment pictured in FIGS. 1, 2 and 5, the introduction section is flared open to an integral target or funnel section 52 between about 1 and 1.75 inches in diameter to facilitate pouring implant material into the first column 30. The inclusion of an integral funnel section 52 makes for an elegant, multi-functional receptacle member. However, due to the threadings which may be molded in such large diameter columns 30 and 36, the mechanical advantage which may be generated by virtue of useable thread pitches is not the most powerful possible.

Where a greater mechanical advantage is desired, the inventive pressure applicator 20 may be configured like the embodiments shown in FIG. 6. In each, the introduction section 24 is only slightly larger than the bore of the vessel section 28 and piston head 26 or seal 50. In the embodiments of FIG. 6 where the introduction section does not include an integral funnel section, the introduction section 24 can be sized about 0.010 to about 0.250 inches over that of the vessel section bore. The introduction section is preferably between about 0.5 in to about 1 inch in height, but may be effective at heights as small as half the thickness of an O-ring being inserted therein, e.g., 0.031 inches. This value, in particular, is driven by the distance of the sealing portion of the plunger 44. For instance, if an O-ring is provided at the very end of the plunger or piston, then the introduction section need only be as high as roughly half the O-ring thickness. The O-ring thickness is preferably about 0.062".

Aside from what provisions may be made for threading or other drive means/mechanism, the shape of the first column 30 exterior to the introduction section 24 is variable. As shown in FIG. 6, the exterior diameter of the first column member may be substantially constant—excepting optimal threads provided. Alternatively, the diameter of the exterior of the first column 30 may follow that of the interior so a substantially constant wall thickness "$T_w$" is employed. The length of threading provided may be varied.

In the pictured embodiments of the invention, the pressure vessel section 28 is advantageously about 0.375 to about 0.75 and preferably about 0.50 inches in diameter in order to have a small enough bore so that the mechanical advantage in applying pressure to the implant material is not overly affected as would be the case with a much larger bore in view of other design parameters. A length for the vessel is between about 1.5 and 3.5 inches so to hold a volume of material between about 4 cc and above 9 cc.

As illustrated in FIG. 6, the embodiments not having an integral funnel section 52 may be used in combination with a separate funnel 54. Where an independent funnel section is used, it may be preferred to use an even larger opening than that of the integrated funnel 52. Funnels with openings of up to about 3 inches would prove useful. Such sizing is reasonable for separate funnels because the exterior of the funnel will not require threadings to interface with a housing member, and consequently, workable size will not be limited by drive means parameters as with the embodiment shown in FIGS. 1, 2 and 5. Departure from a cylindrical profile for an introduction funnel may be advantageous in any embodiment where there will be no threads on the exterior of the funnel.

In embodiments of the invention, it is preferable that the funnel section employed have radiused corners or none at all. A funnel height "$H_f$" of between about 1 and about 4 inches is preferable whether the funnel is integrated into the first column 30 or not. It is preferred that the introduction section have a height "$H_i$" of between about 1.5 and about 2 times over the increase in diameter from the vessel section bore to the introduction section. It is further preferred that implant material to be loaded in the applicator 20 be filled to a level within the range of "$H_i$" to facilitate the purging or venting function of the invention. Filling proceeds to a desired fill level 56 shown in FIG. 2.

Preferable material for the applicator 20 including the first column 30, second column 36 and independent funnel 54 when provided is amorphous nylon. Clear amorphous nylon is preferred for the first column 30 and funnel 52 or 54. The material of the second column 30 may be polished or frosted to the desired fill level 56 to aid in filling with the proper amount of implant material by visual observation of the material. Graduated level marks 58 may also be provided so a quantitative appreciation of the amount of material in the first column 30 may be observed. Of course, alternate material may be useable for the pressure applicator 20 of the invention. Such material includes stainless steel, aluminum or titanium and their alloys, and polymers including, but not limited to, polypropylene and polyvinylchloride (PVC).

To load the applicator 20 of the invention, implant material 46 is poured to or over the desired fill level 56 which is at least part way into the introduction section 24 of the first column 30. The head 26 of the piston or plunger member 44 is then dipped into the implant material where air and excess material flows past the same because of the space provided between the piston head 26 and introduction section 24 walls. Upon further advancement of the piston 44 into the first column 30, a seal is formed with the vessel section wall 60.

Figure 7A:
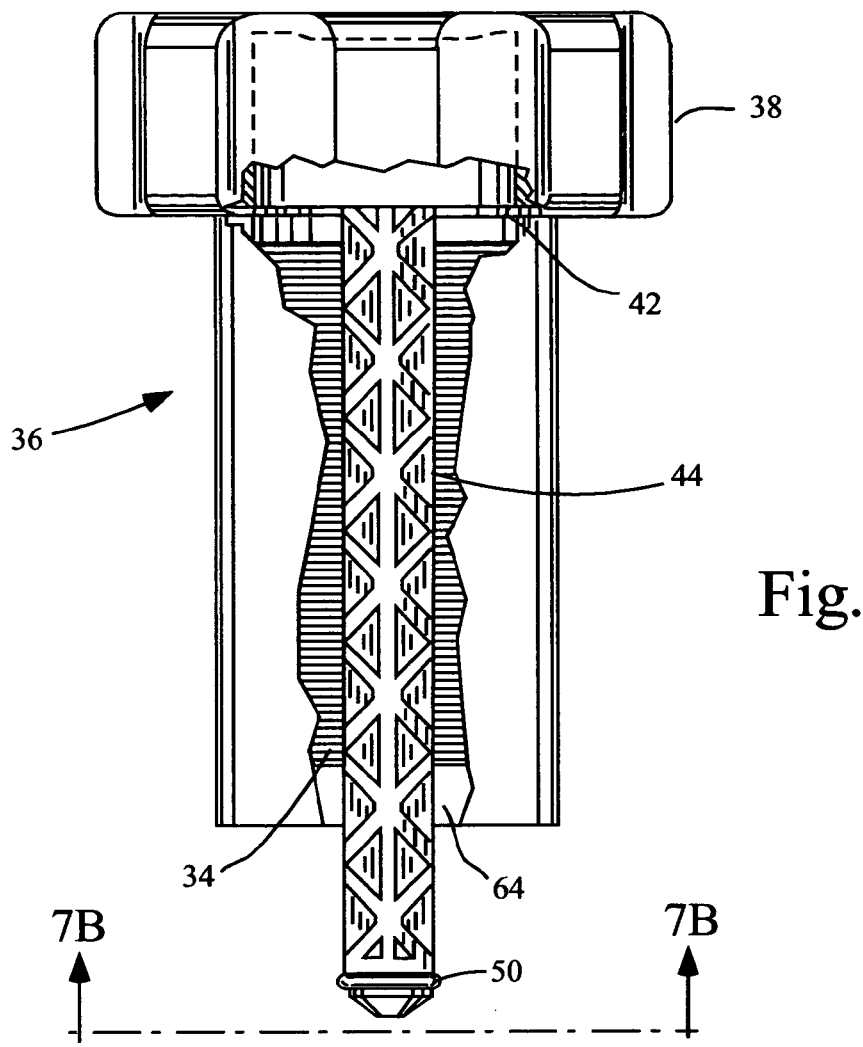
FIGS. 7A, 7B and 7C show views of a housing member, retainer member and plunger.
Figure 7B:
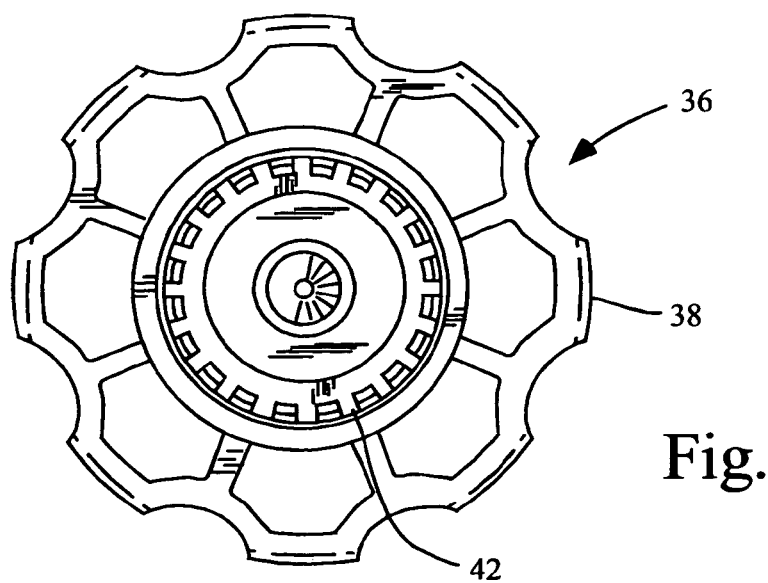
Figure 7C:
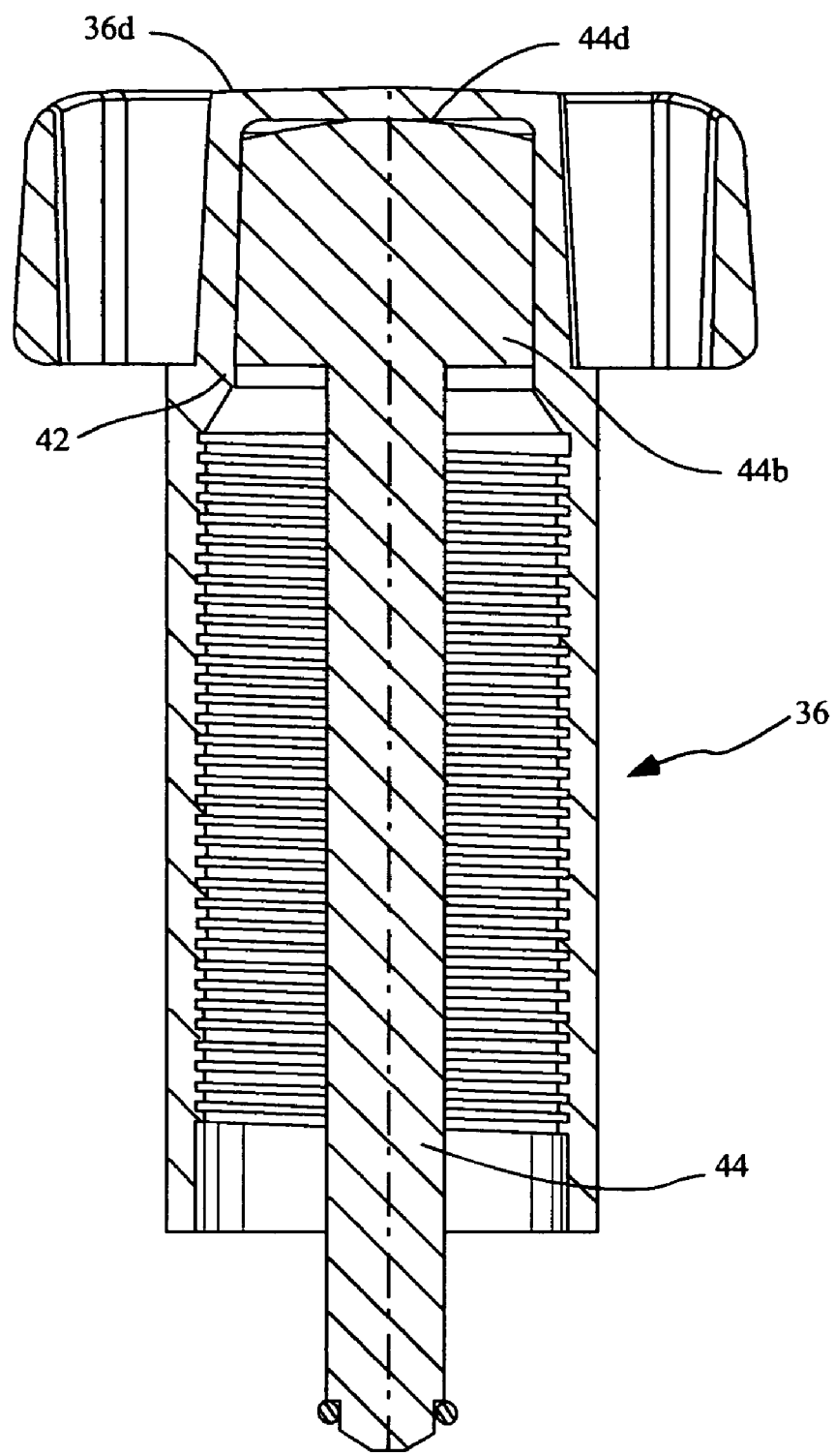

Use of a second column 36 like that shown in FIG. 7A is advantageous in helping provide for such action. A threadbare section 64 is provided here by which threading 32 on the first column 30 may pass thorough without interference. Sliding the threaded section 32 into section 64 not only facilitates dipping the plunger head 26 into material in the introduction section 24 but it aligns the threads 32 and 34 so they may start evenly and avoid becoming "cross threaded." Even where a single-start thread is employed in the invention, the alignment provided by the interaction between section 64 and the first column 30 will be useful in this regard. The bare section 64 is preferably of a length such that a number of threads will be engaged with each other before a seal is formed between the piston 44 or seal 50 and the vessel wall 60.

To form the seal, a separate "sealing" element need not be provided. However, especially where highly viscous materials are concerned, the O-ring or grommet optionally provided is preferred since it can move on the plunger rotationally and thus even if the plunger is turning with the handle, the seal can move independently.

Upon loading of the applicator 20, preferably be inverting it and allowing it to rest on a flat top portion 62, some amount of material may be extruded from the device in order to purge air in the Luer lock 22 or hose 18. The flat configuration of handle 38 also provide a rest upon which the device may be self supported, after filling and threading the device together. It may also be desired to agitate the applicator to keep particles in the implant material evenly dispersed. Since an overabundance of flowable implant material provided in the introduction section during loading will be unconstrained and may foul the exposed threads of the second column 36 upon inversion of the applicator, it is preferable to only fill the introduction section with such an amount of material as required to effectively vent or purge air bubbles as described above.

Following proper loading of the device and such postloading procedures as may be advantageous for a given implant material, delivery of the material to a patient may commence by urging the second column 36 toward the first column 30 and thus the piston 44 into the pressure vessel 28 to force implant material therefrom. In the embodiments shown, such movement will be provided by torque applied by a user to turn the handles 38, 40 relative to each other. Where other drive means are provided (as may be routinely substituted by those with skill in the art), the action required to advance the plunger 44 within the first column will vary but the device and method of use will still be considered to be part of the present invention. Fluoroscopic or other imaging may be used continuously or intermittently during the delivery of the implant material into a patient to monitor the progress of the filling of an implantation site.

Various end-point indicators may be used to indicate that driving of implant material should be discontinued and that the filling procedure has been completed. The particular end point indication method used depends upon a variety of factors, including the characterization of the venous bed within the particular vertebral body being filled, the condition of the bony structure of the vertebral body being filled, and surgeon preference. One end-pointing technique is to simply monitor the filling and terminate driving of the implant material when visual confirmation is made that the body is completely, or nearly-completely filled.

Another end point indicator (which is not necessarily selected by the operator, but is event driven) is when implant material extravasates outside of the vertebral body. This condition may arise due to escape of the implant material through fracture lines, such as when the vertebral body is that of an osteoporitic patient who has suffered a compression fracture. When end pointing is prompted by such an event, the non-compliant aspect of the invention facilitated by effective loading of the device will lessen or eliminate "oozing" or "drip" phenomenon that could result in overfilling the implantation site and the associated dangers.

After filling of the vertebral body has been completed as indicated by one of the endpoint detection indicators described above or others, including those described in U.S. application Ser. No. 09/409,984 referenced above, any remaining pressure is relieve by unthreading the columns ½ to a full turn. The tube 18 is disconnected from the cannula 6, and the cannula is withdrawn. A bandage is typically then applied to the wound site.

Further details as to the use or other aspects of the high-pressure implant system may be noted in the above referenced applications already referred to in describing the present invention or background which are herein incorporated by reference in their entirety. It is noted that this invention has been described and specific examples of the invention have been portrayed. The use of those specific examples is not intended to limit the invention in any way. Additionally, to the extent that there are variations of the invention which are within the spirit of the disclosure and yet are equivalent to the inventions found in the claims, it is the intent that the claims cover those variations as well. All equivalents are considered to be within the scope of the claimed invention, even those which may have not been set forth herein merely for the sake of brevity. Also, the various aspects of the invention described herein may be modified and/or used in combination with such other aspects also described to be part of the invention or disclosed in references discussed to form other advantageous variations considered to be part of the invention covered.

We claim:

1. A method of preparing a high pressure applicator for driving the delivery of a flowable tissue implant material for use, the method comprising;
    providing an applicator having a first column including a vessel section having a bore and an introduction section, a second column drivably engageable with a receptacle member along an advancement axis and a piston member having a base and a piston head;
    filling the first column with implant material over the vessel section and at least partially into the introduction section;
    introducing the head of the piston into the implant material; and
    driving at least the head portion of the piston into the vessel section of the first column to form a high pressure seal between the bore and piston head without the introduction of compliant matter.

2. A method of introducing tissue implant material into a patient, the method comprising:
    preparing the applicator substantially as described in claim 1;
    connecting a noncompliant tube in fluid communication with an outlet of the applicator;
    connecting the tube to an inlet of a cannula in fluid communication with an implantation site; and
    advancing the piston into the bore of the vessel of the first column to force a flow of the implant material into the implantation site.

3. The method of claim 2, wherein said advancement is achieved by hand turning the first and second columns relative to each other along a threaded interface between the columns.

4. The method of claim 2, wherein the first column is stabilized in a substantially constant position and the second column is turned.

5. A method of delivering implant material, the method comprising;
    accessing an implantation site,
    preparing a high pressure applicator as described in claim 1, and
    driving the piston by threadings to force the implant material from the high pressure applicator.

6. The method of claim 5, wherein the implantation site is a vertebral body.

7. The method of claim 1, wherein the receptacle member is integral with said first column.

8. A method of preparing a high pressure applicator for driving the delivery of a flowable tissue implant material, the method comprising:
    providing an applicator comprising a first column and a second column carrying a piston head, the second column drivably engageable by threadings with the first column;
    filling at least a portion of the first column with implant material; and
    introducing the piston head into said first column, wherein air is purged from the implant material upon said introducing.

9. The method of claim 8, wherein the first column includes a vessel section having a bore and an introduction section, and the filling comprises filling the first column with implant material over the vessel section at least partially into the introduction section.

10. The method of claim 8, wherein the implant material is hard tissue implant material.

11. The method of claim 10, wherein the implant material comprises PMMA.

12. A method of delivering implant material, the method comprising;
    accessing an implantation site,
    preparing a high pressure application as described in claim 8, and
    driving the piston head by the threadings to force the implant material from the high pressure applicator.

13. The method of claim 12, wherein the implantation site is a vertebral body.

14. A method of preparing a high pressure applicator for driving the delivery of a flowable tissue implant material for use, the method comprising;
    providing a high pressure applicator having a vessel section having a bore and an introduction section, a piston member comprising a piston head, said piston member drivably engageable with a threaded receptacle member along an advancement axis;
    filling the vessel with the tissue implant material;
    introducing the piston head of the piston member into the implant material; and
    driving at least the piston head of the piston member into the vessel section to form a high pressure seal between the bore and piston head without the introduction of compliant matter.

15. The method of claim 14 wherein said receptacle member is integral with said vessel.

16. The method of claim 14 wherein said tissue implant material is a bone implant material.

* * * * *